United States Patent [19]

Reddy et al.

[11] Patent Number: 5,319,079

[45] Date of Patent: Jun. 7, 1994

[54] PROCESS FOR TERMINAL SUBSTITUTING OF A POLYNUCLEOTIDE

[75] Inventors: Paramesewara M. Reddy, Brea; Serge L. Beaucage, Mountain View, Jang Rampal, Yorbalinda, all of Calif.

[73] Assignee: Beckman Instruments, Inc., Fullerton, Calif.

[21] Appl. No.: 706,549

[22] Filed: May 28, 1991

Related U.S. Application Data

[63] Continuation of Ser. No. 334,759, Apr. 6, 1989, abandoned, which is a continuation of Ser. No. 864,194, May 15, 1986, abandoned.

[51] Int. Cl.$^5$ .............................................. C07H 21/00
[52] U.S. Cl. .................................. 536/25.32; 536/25.4
[58] Field of Search .................. 536/27, 28, 29, 25.32, 536/25.4

[56] References Cited

U.S. PATENT DOCUMENTS

| | | | |
|---|---|---|---|
| 3,440,190 | 4/1969 | Melby et al. | 536/27 |
| 4,286,964 | 9/1981 | Seed | 436/501 |
| 4,302,204 | 11/1981 | Wahl et al. | 436/501 |
| 4,376,820 | 3/1983 | Giannini et al. | 435/4 |
| 4,379,843 | 4/1983 | Cashion | 435/178 |
| 4,483,920 | 11/1984 | Gillespie et al. | 435/6 |
| 4,500,707 | 2/1985 | Caruthers et al. | 536/27 |
| 4,507,433 | 3/1985 | Miller et al. | 525/54.11 |
| 4,542,102 | 9/1985 | Dattagupta et al. | 435/6 |
| 4,556,643 | 12/1985 | Paau et al. | 436/501 |

OTHER PUBLICATIONS

Sekine et al., "4,4',4''-Tris(4,5-dichlorophthalimido)trityl: A New Type of Hydrazine-Labile Group as a Protecting Group of Primary Alcohols," *J. Am. Chem. Soc.*, 106, 5763–5764 (1984).
Kempe et al., "Chemical and Enzymatic Biotin-Labeling of Oligodeoxyribonuclides," *Nucleic Acids Research*, 13(1), 45–57 (1985).
Hakimelahi et al.(I), "Nitrate Ion as Catalyst for Selective Silylations of Nucleosides," *Tett. Lett.*, 22(2), 4775–4778 (1981).
Smith et al., "The Synthesis of Oligonucleotides Containing an Aliphatic Group at the 5'-Terminus: Synthesis of Fluorescent DNA Primers for Use in DNA Sequence Analysis," *Nucleic Acids Research*, 13(7), 2399–2412 (1985).
Ruth, "Chemical Synthesis of Non-Radioactively-Labeled DNA Hybridization Probes," *DNA*, 3(1), 123 (1984).
Bryan et al., "Detection of HBV DNA by Hybridization with Modified Synthetic Oligonucleotides Containing Radioactive and Non-Radioactive Reporter Groups," *DNA*, 3(1), 124 (1984).
Chaudhary et al., "4-Dimethylaminopyridine: An Efficient and Selective Catalyst for the Silylation of Alcohols," *Tett. Lett.*, 1979(2), 99–102.
Chaudhary et al., "A Simplified Procedure for the Preparation of Triphenylmethylethers," *Tett. Lett.*, 1979(2), 95–98.

(List continued on next page.)

*Primary Examiner*—Johnnie R. Brown
*Assistant Examiner*—L. Eric Crane
*Attorney, Agent, or Firm*—William H. May; P. R. Harder; Janis C. Henry

[57] ABSTRACT

Method for substituting a substitution compound for the hydrogen of a support bound primary hydroxyl group. The support bound primary hydroxyl group is treated in an organic, substantially anhydrous solvent in the presence of a tertiary amine base and the substitution compound.

The substitution compound has a positive moiety and a negative moiety. The positive moiety is selected from the group consisting of trityl, pixyl, and derivatives thereof.

The reagent is selected from the group consisting of tetraalkylammonium salts, inorganic salts, and mixtures thereof. Each reagent has a cation and an anion moiety.

The cation moiety of the reagent is more electropositive than the positive moiety of the substitution compound. This relationship enables the reagent to attract the negative moiety of the substitution compound.

15 Claims, 1 Drawing Sheet

OTHER PUBLICATIONS

Gortz et al., "New Hydrophobic Protecting Groups for the Chemical Synthesis of Oligonucleotides," *Angew. Chem. Int. Ed. Engl.*, 20(8), 681–683 (1981).

Seliger et al., "Specific Separation of Products in Supported Oligonucleotide Syntheses Using the Triester Method," *Angew. Chem. Int. Ed. Engl.*, 20(8), 683–684 (1981).

Hakimelahi et al.(II), "New Catalysts and Procedures for the Dimethoxytritylation and Selective Silylation of Ribonucleosides," *Can. J. Chem.*, 60, 1106–1113 (1982).

Chattopadhyaya et al., "The 9-Phenylxanthen-9-yl Protecting Group," *J. Chem. Soc. Chem. Comm.*, 1978, 639–640.

Fieser et al., "Reagents for Organic Synthesis, vol. 1," John Wiley and Sons, Inc., New York, 1967, see pp. 1254–1255.

March, "Advanced Organic Chemistry: Reactions, Mechanisms, and Structure," McGraw-Hill Book Company, 1968, New York, see pp. 327, 559. 618 and 800.

Weber et al., "Phase Transfer Catalysis Part II: Synthetic Applications," *J. Chem. Ed.*, 55(7), 429–433 (1978).

Gait (ed.), "Oligonucleotide Synthesis: A Practical Approach," IRL Press, Washington, DC, 1984, see pp. 12, 13, 27, 28 and 93.

Hinze et al., "Electronegativity. II. Bond and Orbital Electronegativities," *J. Am. Chem. Soc.*, 85, 148–154 (1963).

March, "Advanced Organic Chemistry: Reactions, Mechanisms, and Structure, 3rd Ed.," McGraw-Hill Book Company, 1985, New York, see pp. 218–223.

Gildea et al., "A Versatile Acid Labile Linker for the Solid Phase Preparation of 5′-Functionalized/Labeled Oligodeoxynucleotides," Paper No. 12, San Diego Conference on Nucleic Acid Chemistry, Milligen/Biosearch, Division of Millipore Corporation, Burlington, Mass., published Oct. 25, 1989, see whole document.

Weast et al. (eds.), *CRC Handbook of Chemistry and Physics*, 60th Ed., CRC Press, Inc., Boca Raton, Fla., 1979, p. B-122, see entry S-167.

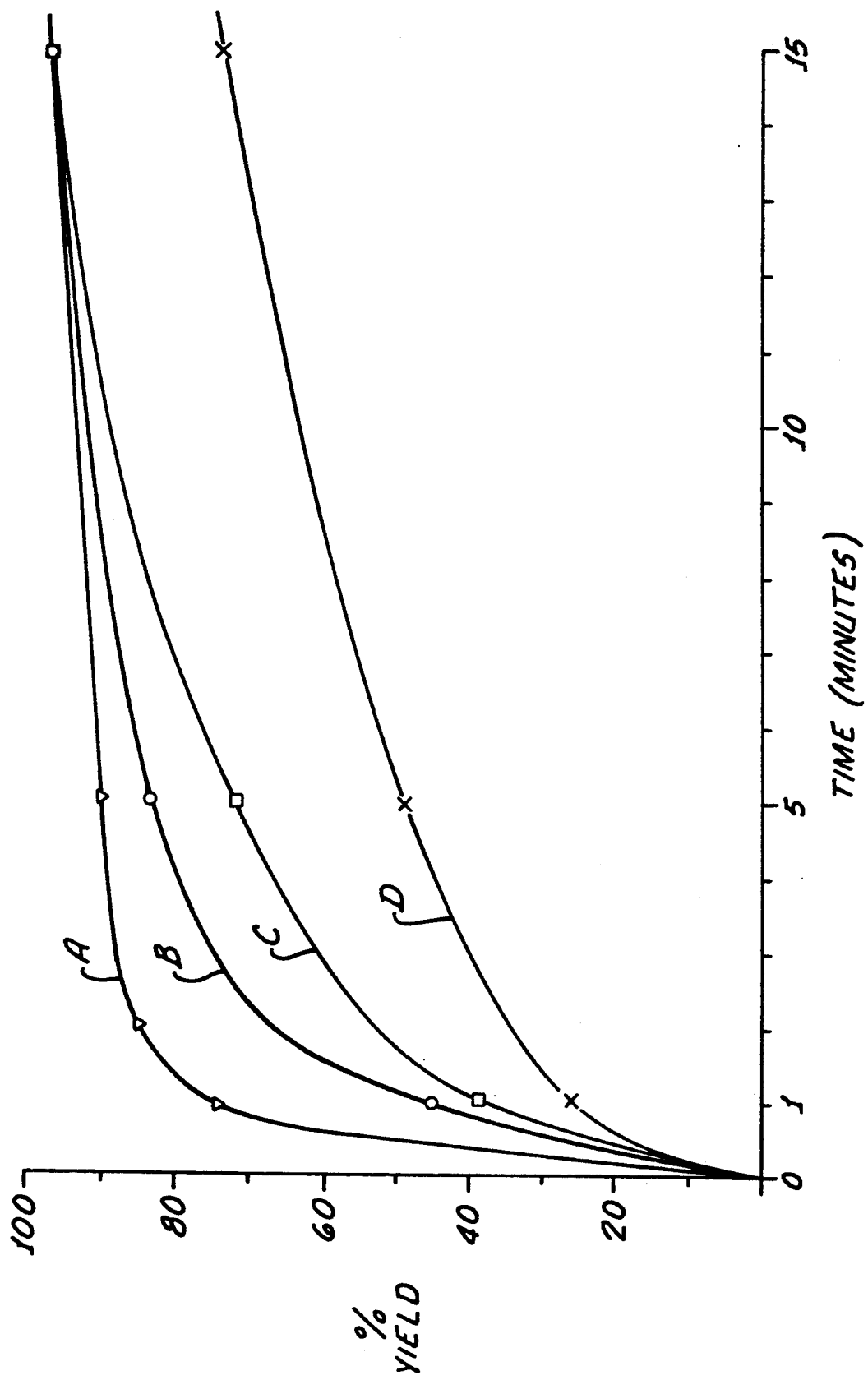

PROCESS FOR TERMINAL SUBSTITUTING OF A POLYNUCLEOTIDE

This is a continuation of application Ser. No. 07/334,759, filed on Apr. 6, 1989, now abandoned, which is a continuation of application Ser. No. 06/864,194, filed May 15, 1986, now abandoned.

BACKGROUND

The present invention relates to a method for substituting trityl, pixyl, and derivatives thereof for the hydrogen of a primary hydroxyl group. More particularly, the invention relates to a method for substituting trityl, pixyl, or derivatives thereof for the hydrogen of a support bound primary hydroxyl group, such as a hydroxyl group of a supported oligonucleotide.

In the chemical synthesis of polynucleotide fragments by the triester procedure, chromatographic methods are important for the purification of protected intermediates and for the isolation of the unprotected final product. The chromatographic behavior of the oligomers can be varied within certain limits by protecting groups, generally producing an unspecific change in the total polarity of the molecule. For example, Gortz et al. Angew. Chem. Int. Ed. Engl., 20(8): 681-683 (1981) describe introducing 4-alkoxytrityl groups for hydrophobic protection at the 5'-end of oligonucleotides. These 4-alkoxytrityl groups contain 8, 10, 12, 14, and 16 carbon atoms. Gortz et al. synthesized 4-hexadecyloxytrityl protected thymidine by first treating 4-hexadecyloxytritanol with acetyl chloride to produce 4-hexadecyloxytrityl chloride. The 4-hexadecyloxytrityl chloride was then treated with thymidine in anhydrous pyridine in the presence of 4-dimethylaminopyridine. After various purification and separation procedures, a 75% yield was obtained. This 4-hexadecyloxytrityl protected thymidine was then condensed onto the 5'—O—position of the terminal nucleotide of a support bound oligonucleotide.

A disadvantage of the procedure of Gortz et al. is that in order to practice this procedure for attaching a hydrophobic protecting group to support bound oligonucleotide, it is necessary to maintain a supply of four separate protected nucleosides, namely, 4-alkoxytrityl protected thymidine, 4-alkoxytrityl protected adenosine, 4-alkoxy protected cytosine, and 4-alkoxytrityl protected guanosine. This is because support bound oligonucleotides can have as a terminal nucleotide any one of these four nucleosides. Accordingly, this requires the outlay of funds for four separate reagents.

A further disadvantage of the Gortz et al. technique is that a 75% yield can be inadequate for many applications.

Moreover, as detailed in the example section below, it has been discovered that the Gortz et al. procedure is ineffective for support bound nucleotides.

Therefore, it would be very desirable if one could obtain a higher yield upon adding the desired group to the nucleoside. It would also be very desirable if a single reagent could be employed when such a group is inserted on the support bound oligonucleotide.

SUMMARY

The present invention provides a process for tritylating or pixylating an oligonucleotide attached to a solid support. The process of this invention uses one reagent and gives relatively high yields.

In accordance with the present invention a hydroxyl group at the 5', 3', or 2' position of the terminal nucleoside of a support bound oligonucleotide can readily be tritylated or pixylated. More particularly, the method of present invention comprises the step of treating the support bound oligonucleotide with a substitution compound in an organic, substantially anhydrous solvent in the presence of a reagent and a tertiary amine base. The substitution compound has a positive moiety and a negative moiety. The positive moiety of the substitution compound is selected from the group consisting of trityl, pixyl, and derivatives thereof. The reagent is selected from the group consisting of tetraalkylammonium salts, inorganic salts and mixtures thereof. The reagent has a cation moiety and an anion moiety. The cation moiety of the reagent is more electropositive than the positive moiety of the substitution compound so that the cation moiety of the reagent is capable of attracting the negative moiety of the substitution compound.

The process of the present invention can also be employed in applications broader than those set forth above. More particularly, the present invention also encompasses a method for substituting a substitution compound for the hydrogen of a support bound primary hydroxyl group. This method comprises the step of treating the support bound primary hydroxyl group with the substitution compound in an organic, substantially anhydrous solvent in the presence of a reagent and a tertiary amine base. The substitution compound, as above, has a positive moiety and a negative moiety. In this embodiment, the positive moiety and reagent are as described above.

In addition to being able to substitute a substitution compound for the hydrogen of a support bound primary hydroxyl group, the hydrogen of a primary hydroxyl of a composition in solution can also be substituted.

DRAWING

These and other features, aspects, and advantages of the present invention will become better understood with reference to the following description, appended claims, and accompanying drawing where:

The single FIG. 1 is a graph comparing the efficacy of various solvents in a tritylation procedure of the present invention.

DESCRIPTION

The present invention is based on the finding that the hydrogen of a support bound primary hydroxyl group can be substituted with a substitution compound in high yields under certain conditions. More particularly, it has been discovered that the hydrogen of a support bound primary hydroxyl group can be substituted with a substitution compound when the support bound hydroxyl group is treated with the substitution compound in an organic, substantially anhydrous solvent in the presence of a particular type of reagent and a particular base.

The substitution compound employed in the substitution process of the present invention has a positive moiety and a negative moiety. The positive moiety is selected from the group consisting of trityl, pixyl, and derivatives thereof. The trityl and pixyl derivatives can have one or more substituents thereon. These substituents can be, for example, alkyl, alkoxy, amino, aminoalkyl, aminoalkoxy, thio, thioalkyl, thioalkoxy, hydroxyl, and hydroxylalkyl. The length of the alkyl and alkoxy moiety are such that the substitution compound can remain in solution in an organic solvent. In general, such alkyl and alkoxy groups can contain from about 1 to about 24 carbon atoms. Reactive substituents (e.g., amino, thio, aminoalkyl, aminoalkoxy, thioalkyl, thioalkoxy, etc.) can, in turn, be attached to a marker. A marker is a detectable substance. Typical markers include, but are not limited to, enzymes, antigens, antibodies, biotin, avidin, fluorescent compositions, bioluminescent compositions, chemiluminescent compositions, and radioactive compositions. The marker can be attached to the reactive substituents of the substitution compound either before or after the substitution compound is substituted for the hydrogen of the nucleotide's unprotected primary hydroxyl group.

By using multifunctional trityl groups like rosolic acid [tris(4-hydroxyphenyl)methanol] and pararosaniline [tris(4-aminophenyl)methanol] one can place several substituents (e.g., hydrophobic groups) on the trityl or pixyl group. Such substituted trityl and pixyl groups, with or without markers attached thereto, can subsequently be substituted for the hydrogen of a primary hydroxyl group.

There are several ways to place the reactive substituent on the trityl or pixyl group. One scheme for attaching reactive groups to trityl is as follows:

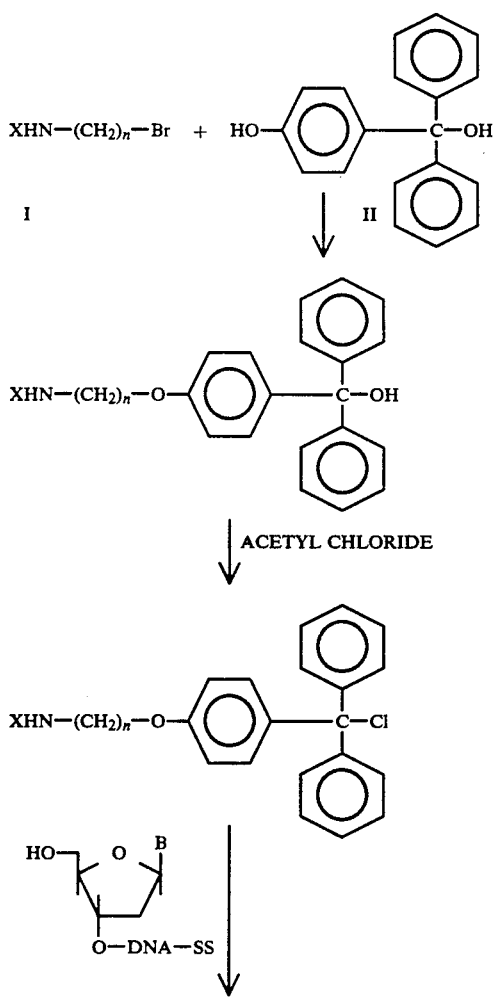

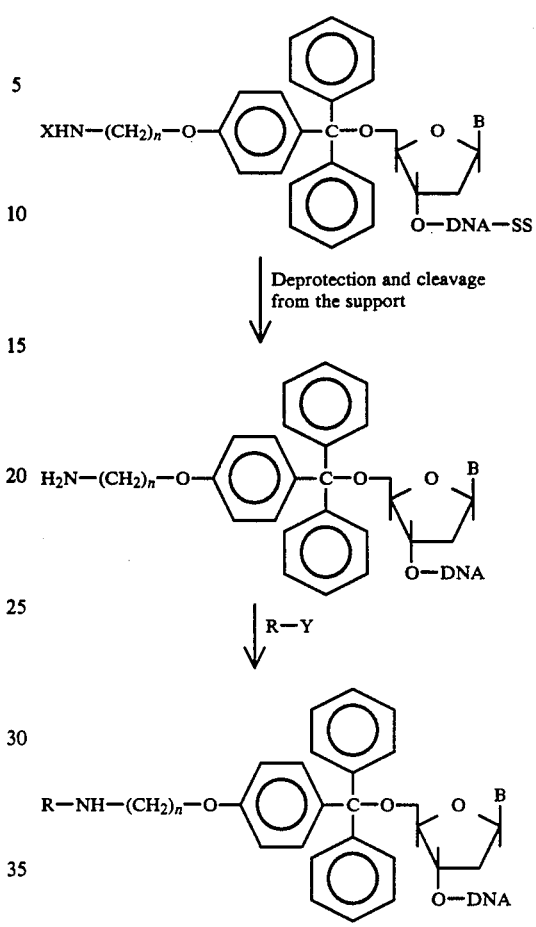

In the above procedure, (p-hydroxyphenyl)diphenylmethanol (II) can be alkylated with a suitably protected aminoalkylbromide, where n is at least 1. The protecting group X of the amino function can be a suitable amino protecting group, e.g., halogenoacetyl phthaloyl, FMOC, etc. The tritanol can be converted to a trityl chloride and subsequently be substituted for the hydrogen of a primary hydroxy group using the procedure of the present invention.

The amino group can be deprotected using appropriate conditions. See Green, *Protective Groups in Organic Synthesis*, John Wiley & Sons (1981). For example, $NH_4OH$ which is normally used for cleaving the oligonucleotide from the solid support (SS) can also remove the acetyl or halogenoacetyl group. Piperidine can remove the FMOC group and hydrazine ($H_2NNH_2$) can remove the phthaloyl group.

Several non-radioactive markers (R), such as fluorescein, dinitrobenzene, and biotin, can be attached to the amino function of the tritylated or pixylated oligonucleotide using the procedure of Ruth, *DNA*, 5: 123 (1984). Ruth used such marked oligodeoxyribonucleotides (DNA) as non-radioactive hybridization probes.

Similiarly, different fluorescent groups can be attached to the amino function. See Smith et al., *Nucleic Acids Research*, 13 (7): 2399-2412 (1985). Smith et al. used the fluorescent derivatives of oligonucleotides in DNA sequence analysis.

As illustrated in the above schematic procedure, the marker R is attached to Y. Y is a good leaving group.

Good leaving groups include, but are not limited to p-nitrophenoxy and N-hydroxysuccinyl.

By using multifunctional trityl groups like rosolic acid and pararosaniline, one can attach several markers on the oligonucleotide. It is also possible to attach the marker directly to the hydroxy and amino functions of rosolic acid and pararosaniline, respectively, prior to tritylating the hydroxyl group. The following schematic procedures illustrate how this can be accomplished with parosaniline:

General Scheme

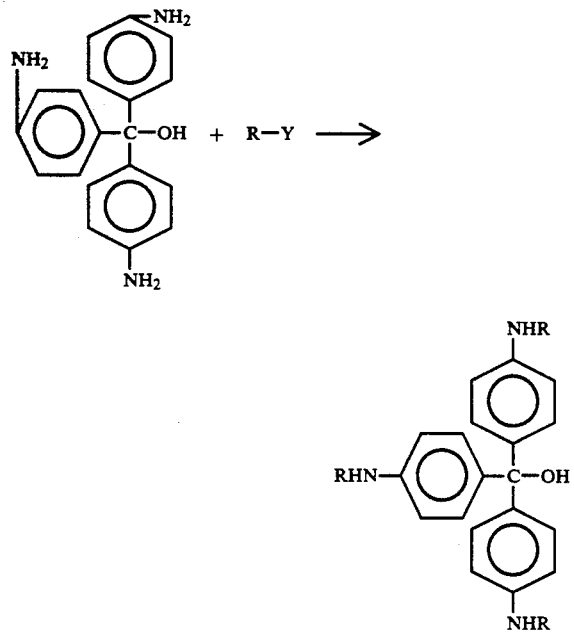

Biotin or Fluorescein (X)

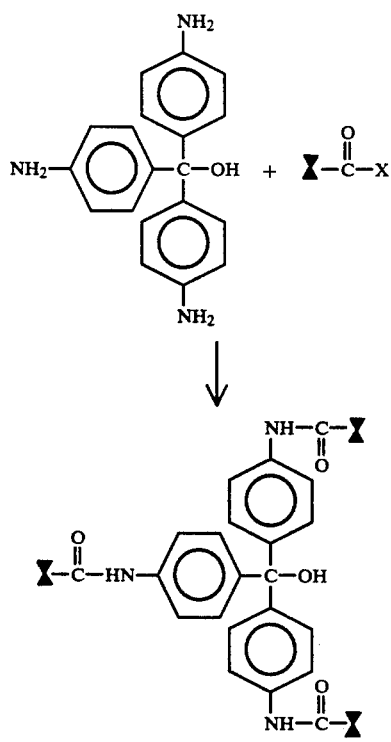

Meta-dinitrophenyl

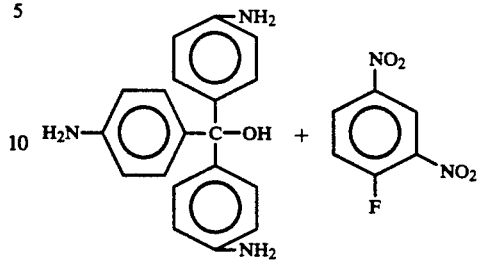

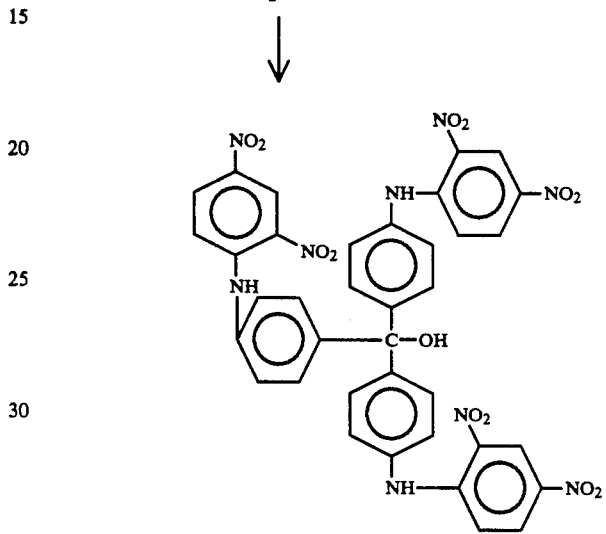

The reagents employed in the substitution procedure of the present invention are selected from the group consisting of tetraalkylammonium salts, inorganic salts, and mixtures thereof. Each reagent has a cation moiety and an anion moiety.

The tetraalkylammonium salts and inorganic salts must be soluble in the organic solvent employed in the process of this invention. Accordingly, the alkyl moieties of the tetraalkylammonium salts are selected such that the resulting tetraalkylammonium salt is soluble in the particular solvent chosen for use in the process of this invention. Exemplary alkyl groups can contain from 1 to about 20 carbon atoms. Commercially available tetraalkylammonium salts have alkyl groups containing from about 2 to about 5 carbon atoms.

The anion moiety of the tetraalkylammonium salt preferably is selected from the group consisting of nitrate, sulfate, perchlorate, and iodide.

As noted above, the inorganic salt must be soluble in the organic solvent used in the substitution process. Accordingly, the cation and anion moieties of the inorganic salt are chosen in view of this criteria. Exemplary cation moieties of the inorganic salt include, but are not limited to, silver, ferrous, and lead. Exemplary anion moieties of the inorganic salt include, but are not limited to, nitrate, halide, sulfate, and perchlorate. The halide is preferably bromide.

For the substitution process of the present invention to proceed efficiently, it is essential that the cation moiety of the reagent be more electropositive than the positive moiety of the compound so that the cation moiety of the reagent is capable of attracting the negative moiety of the substitution compound. One can determine the relative electropositive characteristics of these moieties by placing a potential reagent and potential substitution compound in an anhydrous organic solvent and a tertiary amine base and determining whether the hydrogen of the primary hydroxyl group is substituted by the positive moiety of the substitution compound.

It is also desirable that the anion moiety of the reagent be less electronegative than the negative moiety of the substitution compound.

The organic, substantially anhydrous solvent, is selected from the group consisting of pyridine, methylene, chloride, dimethylformamide, dioxan, tetrahydrofuran, and trialkylamine. Commercially available trialkylamines have alkyl groups containing from 1 to about 6 carbon atoms. The organic, substantially anhydrous solvent can also be an aprotic solvent.

The base can be any tertiary amine. Tertiary amine bases include, but are not limited to, trialkylamine, collidine, pyridine, and lutidine.

Since the solvent and base can both be pyridine and trialkylamine, it should be understood that, the solvent and base are the same composition.

The substitution process of the present invention can be performed on any primary hydroxyl group that is attached to a support. Such primary hydroxyl groups can be found on polymers like carbohydrates (cellulose, agarose, etc.) as well as on the terminal nucleotide of a support bound oligonucleotide.

With respect to support bound oligonucleotides, the terminal nucleotide of the support bound oligonucleotide can have a primary hydroxyl group at its 5', 3', or 2' position. When the terminal nucleotide is a deoxyribonucleotide, the primary hydroxyl group can be located at either the 5' or 3' position. When the terminal nucleotide is a ribonucleotide, the primary hydroxyl group can be located at either the 5', 3', or 2' position. The support bound oligonucleotide can contain one or more nucleotides.

Because the majority of the oligonucleotide synthesis involves the condensation of a nucleoside through its 3'-O- position to the 5'-O- position of the terminal nucleotide of the support bound oligonucleotide, the present invention has significant application in the substitution of the hydrogen at the 5'-O- of the terminal nucleotide of the support bound oligonucleotide.

In general, the substitution procedure of the present invention requires from about a minute or less to several hours or more. In general, it has been found that satisfactory results can be obtained when the substitution procedure is conducted for about 30 seconds to about 1 hour. More preferably, the substitution reaction is conducted for about 1 to about 10 minutes. Very satisfactory results were obtained when the substitution procedure was conducted for about 5 minutes.

The substitution reaction can be conducted at any convenient temperature. Satisfactory results were obtained when the substitution reaction was conducted at room temperature. If one wishes to have the substitution procedure proceed at a faster rate, an elevated reaction temperature can be used. Conversely, if a slower rate reaction is desired, a lower temperature can be used.

The amount of substitution compound employed can vary. In general, the molar ratio of substitution compound to oligonucleotide is at least about 1 to 1. Preferably, a large excess of compound is employed.

The amount of substitution reagent employed is a function of the amount of substitution compound employed. In general, a sufficient amount of reagent is employed so that substantially all of the anions of the substitution compound are attracted to the reagent. When the cation moiety of the reagent is only capable of attracting one negative moiety of the substitution compound, then preferably substantially equal molar amounts of substitution compound and reagents are employed.

The relative concentrations of the base and compound can vary and depend on the number of tertiary amine present in the base. If the base has only one tertiary amine, then it is preferred that at least an equivalent amount of base be used per mole of compound. Preferably, in such instance about 1.5 equivalent base be used per mole of compound.

When the base contains 2 or more tertiary amine groups per molecule and each tertiary amine group is separated from the others by at least one carbon atom, then a lesser amount (about 1/m) of tertiary amine base can be used, wherein m is the number of such tertiary amine groups per molecule of base.

EXAMPLES

In the following examples, the efficacy of the substitution process of the present invention is demonstrated. The examples also show the efficacy of various solvents in a process of the present invention.

EXAMPLE 1

This example demonstrates that the Gortz et al. process is ineffective for a support bound nucleotide.

A thymidine attached to a controlled pored glass (CPG) support and having a 5' hydroxyl group on the terminal nucleotide was treated with a tritylating agent in a solvent in the presence of a reagent. The reaction conditions and results of this experiment are set forth in Table I.

TABLE I

| TRITYLATING AGENT | CONCENTRATION | REAGENT (EQUIVALENT) | SOLVENT | HOURS | YIELD PERCENT (%) |
|---|---|---|---|---|---|
| 4, 4'-Dimethoxytrityl Chloride | 0.5M | 4-N, N'-Dimethyl-aminopyridine(1) | Pyridine | 2 | 9 |
| 4, 4'-Dimethoxytrityl Chloride | 0.5M | 4-N, N'-Dimethyl-aminopyridine(1) | Pyridine | 60 | 32 |

As shown in Table I, the attempt to tritylate the 5'-hydroxyl of thymidine attached to the CPG support by using dimethoxytrityl chloride and 4-N, N'-dimethylaminopyridine gave very poor yields. Accordingly, it appeared that the prior art method employed to tritylate nucleosides in solution is not readily transposable for purposes of tritylating a nucleoside attached to a solid support.

EXAMPLE 2

Tritylation Procedure Employing Silver Nitrate

A trityl solution was prepared by dissolving tritylbromide (0.5M) and silver nitrate (1 equivalent) in dimethylformamide (DMF) and adding collidine (1.5 equivalents) thereto. The controlled pored glass (CPG) support to which the nucleoside was attached through its 3'-linkage was washed with dry methylene chloride. The trityl solution was added to the washed support under dry conditions. After 4 hours, the trityl solution was washed off with methylene chloride. A quantitative yield was obtained.

EXAMPLE 3

Tritylation Procedure Employing Silver Nitrate

A trityl solution was prepared by dissolving 4, 4'-dimethoxytrityl chloride (0.5M) and silver nitrate (1 equivalent) dissolved in dry DMF and adding collidine (1.5 equivalents) thereto. The CPG support to which the nucleoside was attached through its 3'-linkage was washed with dry methylene chloride. The trityl solution was added to the washed support under dry conditions. After one minute, the trityl solution was washed off with methylene chloride. The absorbance of 4, 4'-dimethoxytrityl cation released by treatment with 2 percent volume/volume dichloroacetic acid was measured at 500 nm. A quantitative yield was obtained.

EXAMPLE 4

Comparative Solvent Efficacy

A trityl solution was prepared by dissolving 4, 4'-dimethoxytritylchloride (0.5M) and tetrabutylammonium nitrate (1 equivalent) in various solvents and adding collidine (1.5 equivalents) thereto. The CPG support to which a guanosine protected nucleoside was attached through its 3'-linkage was washed with dry solvent. The trityl solution was added to the washed support under dry conditions. The results of this kinetic study are plotted in FIG. 1.

BRIEF DESCRIPTION OF THE FIGURE

In FIG. 1, the solvent used in generating curve A was methylene chloride; a 1 to 1 volume/volume solution of tetrahydrofuran and methylene chloride was used in generating curve B; DMF was employed in generating curve C; and dioxan was employed in the procedure which gave rise to curve D. As shown in FIG. 1, the substitution process proceeded the fastest in the methylene chloride and the slowest in dioxan.

EXAMPLE 5

Tritylation Procedure Employing Various Tetrabutylammonium Salts

A trityl solution was prepared by dissolving 4, 4'-dimethoxytrityl chloride (0.5M) and a tetrabutylammonium salt (1 equivalent) in dry methylene chloride and adding collidine (1.5 equivalents) thereto. The CPG support to which the nucleoside was attached through its 3'-linkage was washed with dry methylene chloride. The trityl solution was added to the washed support under dry conditions. After 5 minutes, the trityl solution was washed off with methylene chloride. The absorbance of 4, 4'-dimethoxytrityl cation released by treatment with 2 percent volume/volume dichloroacetic acid was measured at 500 nm. The results of this study are set forth in Table II.

TABLE II

Tritylation of CPG Bound $G^{ibu*}$ with 4, 4'-Dimethoxytrityl Chloride

| REAGENT | Tritylated Product Obtained in 5 Minutes, Percent (%) |
| --- | --- |
| Tetrabutylammonium Nitrate | 90 |
| Tetrabutylammonium Hydrogen Sulfate | 73 |
| Tetrabutylammonium Perchlorate | 97 |
| Tetrabutylammonium Iodide | 85 |

*$G^{ibu}$ denotes $-\overset{O}{\underset{\|}{C}}$-isobutyl protected guanosine As shown in Table II, one can substitute a compound for the hydrogen of a primary hydroxyl group bound to a solid support and obtain relatively good yields in accordance with the procedure of the present invention as exemplified in this example.

EXAMPLE 6

Tritylation of Various Bases

A trityl solution was prepared by dissolving 4, 4'-dimethoxytrityl chloride (0.5M) and tetrabutylammonium perchlorate (1 equivalent) in dry methylene chloride and adding collidine (1.5 equivalents) thereto. The CPG support to which a nucleoside was attached through its 3'-linkage was washed with dry methylene chloride. The trityl solution was added to the washed support under dry conditions. After 5 minutes the trityl solution was washed off with methylene chloride. The absorbance of 4, 4'-dimethoxytrityl cation released by treatment with 2 percent volume/volume dichloroacetic acid was measured at 500 nm.

The above procedure was employed with 4 different nucleosides, namely thymidine (T), guanosine ($G^{ibu}$), adenosine ($A^{bz}$), and cytosine ($C^{bz}$), wherein bz denotes $$-\overset{O}{\underset{\|}{C}}-\text{O}.$$

Quantitative yields were obtained in each instance.

EXAMPLE 7

Tritylation of Fully Protected Oligodeoxyribonucleotide

GATCTAGAGCTCGAGCTCTA-CPG

Tritylation of the 5'-hydroxyl of the above fully protected oligodeoxyribonucleotide gave 90 percent tritylation product in 5 minutes. The yield did not increase significantly even after treatment for several hours. This finding suggested that the substitution procedure of this invention occurs only with the unprotected hydroxyl group. To confirm this finding, nucleoside monomers $T_{oac}$, $G_{obz}{}^{ibu}$, $A_{obz}{}^{bz}$, $C_{obz}{}^{bz}$ were treated with an excess of tritylating agent for several hours, wherein oac denotes $$-\overset{O}{\underset{\|}{C}}-CH_3;$$

obz denotes

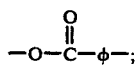

and ibu and bz are as defined above. Thin layer of chromatography (TLC) analysis showed only products corresponding to 5'-tritylation. Accordingly, this experiment confirms that the substitution procedure of this invention only occurs with the unprotected hydroxyl group.

Although the present invention has been described in considerable detail with reference to certain versions thereof, other versions are possible. For example, the hydrogen of a primary hydroxyl group of a composition in solution can also be substituted via the process of the present invention. In this embodiment, the reagent is selected from the group consisting of tetraalkylammonium salts and mixtures thereof. The reason this embodiment is feasible is that a substitution procedure is more difficult to perform when the primary hydroxyl group is attached to a solid support. Accordingly, if a substitution procedure can be performed on a primary hydroxyl group bound to a solid support, such procedure would analogously proceed with a primary hydroxyl group of a composition that is in solution. Accordingly, the spirit and scope of the appended claims should not be limited to the description of the preferred versions contained herein.

What is claimed is:

1. A process for substituting a reactive hydrophobic organic moiety for hydrogen at the 5'—O— position of the terminal nucleotide of a support bound oligonucleotide, the process comprising the step of combining the support bound oligonucleotide with a reactive hydrophobic organic halide in an organic, substantially anhydrous solvent in the presence of a reagent and a tertiary amine base under substantially anhydrous conditions, wherein:
   (a) the reactive hydrophobic organic halide consists of the reactive hydrophobic organic moiety and a halogen moiety, the reactive hydrophobic moiety being selected from the group consisting of trityl and pixyl moieties;
   (b) the 5'—O— position of the terminal nucleotide becomes attached to the saturated, tertiary carbon of the reactive hydrophobic organic moiety;
   (c) the reagent is present in an amount sufficient to attach to substantially all of the halogen moiety of the reactive hydrophobic organic halide, and the reagent is selected from the group consisting of tetraalkyl ammonium salts, the reagent having a cation moiety consisting of a tetraalkylammonium ion wherein the alkyl groups contain from 1 to about 20 carbon atoms and an anion moiety; and
   (d) the cation moiety of the reagent is more electropositive than the reactive hydrophobic organic moiety of the reactive hydrophobic organic halide so that the cation moiety of the reagent is capable of attracting the halogen moiety of the reactive hydrophobic organic halide.

2. The process of claim 1 wherein the oligonucleotide is a oligodeoxyribonucleotide.

3. The process of claim 1 wherein the solvent is the base.

4. The process of claim 1 wherein the solvent is selected from the group consisting of pyridine, methylene chloride, dimethylformamide, dioxan, tetrahydrofuran, and trialkylamine, wherein each alkyl group of the trialkylamine contains 1 to about 6 carbon atoms.

5. The process of claim 1 wherein the solvent is an aprotic solvent.

6. The process of claim 1 wherein the base is selected from the group consisting of trialkylamine, collidine, pyridine, and lutidine, wherein the each alkyl group of the trialkylamine contains 1 to about 6 carbon atoms.

7. The process of claim 6 wherein each alkyl group of the trialkylamine contains about 2 to about 3 carbon atoms.

8. The process of claim 4 wherein each alkyl group of the trialkylamine contains about 2 to about 3 carbon atoms.

9. The process of claim 1 wherein the anion moiety of the reagent is more electropositive than the halogen moiety of the reactive hydrophobic organic halide.

10. The process of claim 1 wherein the alkyl groups of the tetraalkylammonium salt consists of from 1 to about 10 carbon atoms.

11. The process of claim 1 wherein the alkyl groups of the tetraalkylammonium salt consists of from about 2 to about 6 carbon atoms.

12. The process of claim 1 wherein the anion moiety of the tetraalkylammonium salt is selected from the group consisting of nitrate, sulfate, perchlorate, and iodide.

13. The process of claim 1 wherein the tetraalkylammonium salt is tetrabutylammonium nitrate.

14. The process of claim 1 wherein the tetraalkylammonium salt is tetraalkylammonium perchlorate.

15. The process of claim 1 wherein the tetraalkylammonium salt is tetrabutylammonium iodide.

* * * * *